US008808327B2

(12) United States Patent
Yuan et al.

(10) Patent No.: US 8,808,327 B2
(45) Date of Patent: *Aug. 19, 2014

(54) DEVICE FOR SECURING SPINAL RODS (71) Applicant: Howmedica Osteonics Corp., Mahwah, NJ (US)

(72) Inventors: Hansen Yuan, Fayetteville, NY (US); David Nichols, Trumbull, CT (US); Eric Finley, San Diego, CA (US)

(73) Assignee: Howmedica Osteonics Corp., Mahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/653,751

(22) Filed: Oct. 17, 2012

(65) Prior Publication Data
US 2013/0041411 A1 Feb. 14, 2013

Related U.S. Application Data (60) Continuation of application No. 12/827,230, filed on Jun. 30, 2010, now Pat. No. 8,313,510, which is a division of application No. 10/091,708, filed on Mar. 6, 2002, now Pat. No. 7,780,703, which is a division of application No. 09/487,942, filed on Jan. 19, 2000, now Pat. No. 6,565,565, which is a continuation-in-part of application No. 09/098,927, filed on Jun. 17, 1998, now Pat. No. 6,090,111, and a continuation-in-part of application No. 09/167,439, filed on Oct. 6, 1998, now abandoned.

(51) Int. Cl.
*A61B 17/70* (2006.01)
(52) U.S. Cl.
USPC .......................................... 606/246

(58) Field of Classification Search
USPC ......... 606/246, 264–268, 270, 272–275, 279, 606/301, 305, 308, 328; 623/17.11, 17.14; 403/362; 411/393
See application file for complete search history.

(56) References Cited

U.S. PATENT DOCUMENTS

| 1,956,745 A | 5/1934 | Payne |
| 3,352,344 A | 11/1967 | Lanius, Jr. |

(Continued)

FOREIGN PATENT DOCUMENTS

| CA | 2215485 A1 | 9/1996 |
| CA | 2206853 A1 | 12/1997 |

(Continued)

OTHER PUBLICATIONS

European Search Report dated Feb. 10, 2000.
European Search Report dated Jan. 19, 1999.
European Search Report dated Oct. 2, 2000.
Opinion, Case 2:05-cv-00041-GJQ, Document 81, Filed Oct. 13, 2005, US District Court for the Western District of Michigan Northern Division, pp. 1-18.

(Continued)

*Primary Examiner* — Pedro Philogene
*Assistant Examiner* — David Comstock
(74) *Attorney, Agent, or Firm* — Lerner, David, Littenberg, Krumholz & Mentlik, LLP (57) ABSTRACT A device is disclosed for securing a spinal rod to the spine which includes a head portion configured to receive a spinal rod, a locking cap configured to engage the head portion and the spinal rod upon rotation of the locking cap relative to the head portion to secure the position of the head portion relative to the spinal rod, and a fastener portion depending from the head portion and configured to engage the spine. The locking cap has discontinuous opposed engagement flanges that are received within opposed engagement slots of the head portion when the locking cap is rotated into a locked position.

23 Claims, 11 Drawing Sheets

(56) References Cited

U.S. PATENT DOCUMENTS

| | | |
|---|---|---|
| 3,961,854 A | 6/1976 | Jaquet |
| 4,269,178 A | 5/1981 | Keene |
| 4,498,263 A | 2/1985 | Bocker |
| 4,641,636 A | 2/1987 | Cotrel |
| 4,805,602 A | 2/1989 | Puno et al. |
| 4,815,453 A | 3/1989 | Cotrel |
| 4,887,596 A | 12/1989 | Sherman |
| 4,946,458 A | 8/1990 | Harms et al. |
| 5,005,562 A | 4/1991 | Cotrel |
| 5,010,879 A | 4/1991 | Moriya et al. |
| 5,074,864 A | 12/1991 | Cozad et al. |
| 5,102,412 A | 4/1992 | Rogozinski |
| 5,112,332 A | 5/1992 | Cozad et al. |
| 5,116,334 A | 5/1992 | Cozad et al. |
| 5,176,678 A | 1/1993 | Tsou |
| 5,176,680 A | 1/1993 | Vignaud et al. |
| 5,181,917 A | 1/1993 | Rogozinski |
| 5,190,543 A | 3/1993 | Schlapfer |
| 5,207,678 A | 5/1993 | Harms et al. |
| 5,217,497 A | 6/1993 | Mehdian |
| 5,257,993 A | 11/1993 | Asher et al. |
| 5,261,912 A | 11/1993 | Frigg |
| 5,281,222 A | 1/1994 | Allard et al. |
| 5,334,203 A | 8/1994 | Wagner |
| 5,346,493 A | 9/1994 | Stahurski et al. |
| 5,360,431 A | 11/1994 | Puno et al. |
| 5,368,594 A | 11/1994 | Martin et al. |
| 5,380,326 A | 1/1995 | Lin |
| 5,385,583 A | 1/1995 | Cotrel |
| 5,437,669 A | 8/1995 | Yuan et al. |
| 5,437,670 A | 8/1995 | Sherman et al. |
| 5,437,671 A | 8/1995 | Lozier et al. |
| 5,439,463 A | 8/1995 | Lin |
| 5,443,467 A | 8/1995 | Biedermann et al. |
| 5,466,237 A | 11/1995 | Byrd, III et al. |
| 5,474,555 A | 12/1995 | Puno et al. |
| 5,476,462 A | 12/1995 | Allard et al. |
| 5,496,321 A | 3/1996 | Puno et al. |
| 5,498,263 A | 3/1996 | DiNello et al. |
| 5,507,746 A | 4/1996 | Lin |
| 5,520,689 A | 5/1996 | Schlapfer et al. |
| 5,520,690 A | 5/1996 | Errico et al. |
| 5,545,167 A | 8/1996 | Lin |
| 5,549,608 A | 8/1996 | Errico et al. |
| 5,554,157 A | 9/1996 | Errico et al. |
| 5,562,663 A | 10/1996 | Wisnewski et al. |
| 5,584,833 A | 12/1996 | Fournet-Fayard et al. |
| 5,591,165 A | 1/1997 | Jackson |
| 5,591,166 A | 1/1997 | Bernhardt et al. |
| 5,613,968 A | 3/1997 | Lin |
| 5,615,965 A | 4/1997 | Saurat et al. |
| 5,624,440 A | 4/1997 | Huebner |
| 5,628,740 A | 5/1997 | Mullane |
| 5,630,817 A | 5/1997 | Rokegem et al. |
| 5,643,260 A | 7/1997 | Doherty |
| 5,647,873 A | 7/1997 | Errico et al. |
| 5,667,508 A | 9/1997 | Errico et al. |
| 5,669,911 A | 9/1997 | Errico et al. |
| 5,672,176 A | 9/1997 | Biedermann et al. |
| 5,683,390 A | 11/1997 | Metz-Stavenhagen et al. |
| 5,683,392 A | 11/1997 | Richelsoph et al. |
| 5,685,394 A | 11/1997 | Simson et al. |
| 5,690,630 A | 11/1997 | Errico et al. |
| 5,697,929 A | 12/1997 | Mellinger |
| 5,702,393 A | 12/1997 | Pfaifer |
| 5,702,395 A | 12/1997 | Hopf |
| 5,716,355 A | 2/1998 | Jackson et al. |
| 5,716,356 A | 2/1998 | Biedermann et al. |
| 5,725,527 A | 3/1998 | Biedermann et al. |
| 5,728,098 A | 3/1998 | Sherman et al. |
| 5,733,285 A | 3/1998 | Errico et al. |
| 5,733,286 A | 3/1998 | Errico et al. |
| 5,738,685 A | 4/1998 | Halm et al. |
| 5,752,957 A | 5/1998 | Ralph et al. |
| 5,782,833 A | 7/1998 | Haider |
| 5,791,911 A | 8/1998 | Fasano et al. |
| 5,797,911 A | 8/1998 | Sherman et al. |
| 5,817,094 A | 10/1998 | Errico et al. |
| 5,863,293 A | 1/1999 | Richelsoph |
| 5,873,878 A | 2/1999 | Harms et al. |
| 5,879,350 A | 3/1999 | Sherman et al. |
| 5,882,350 A | 3/1999 | Ralph et al. |
| 5,885,286 A | 3/1999 | Sherman et al. |
| 5,891,145 A | 4/1999 | Morrison et al. |
| 5,910,142 A | 6/1999 | Tatar |
| 5,928,233 A | 7/1999 | Apfelbaum et al. |
| 5,954,725 A | 9/1999 | Sherman et al. |
| 5,961,517 A | 10/1999 | Biedermann et al. |
| 5,964,760 A | 10/1999 | Richelsoph |
| 5,989,254 A | 11/1999 | Katz |
| 6,010,503 A | 1/2000 | Richelsoph et al. |
| 6,030,388 A | 2/2000 | Yoshimi et al. |
| 6,053,917 A | 4/2000 | Sherman et al. |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,077,263 A | 6/2000 | Ameil et al. |
| 6,090,111 A * | 7/2000 | Nichols ............... 606/266 |
| 6,100,172 A | 8/2000 | Furukawa et al. |
| 6,110,172 A | 8/2000 | Jackson |
| 6,139,549 A | 10/2000 | Keller |
| 6,146,383 A | 11/2000 | Studer et al. |
| 6,171,311 B1 | 1/2001 | Richelsoph |
| 6,258,090 B1 | 7/2001 | Jackson |
| 6,264,658 B1 | 7/2001 | Lee et al. |
| 6,302,888 B1 | 10/2001 | Mellinger et al. |
| RE37,479 E | 12/2001 | Kuslich |
| 6,371,957 B1 | 4/2002 | Amrein et al. |
| 6,565,565 B1 * | 5/2003 | Yuan et al. ............ 606/272 |
| 6,585,737 B1 | 7/2003 | Baccelli et al. |
| 7,608,095 B2 | 10/2009 | Yuan et al. |
| 7,780,703 B2 * | 8/2010 | Yuan et al. ............ 606/246 |
| 7,819,901 B2 * | 10/2010 | Yuan et al. ............ 606/264 |
| 8,313,510 B2 * | 11/2012 | Yuan et al. ............ 606/246 |
| 2002/0007183 A1 | 1/2002 | Lee et al. |

FOREIGN PATENT DOCUMENTS

| | | |
|---|---|---|
| DE | 653799 C | 12/1937 |
| DE | 9403231 U1 | 4/1994 |
| EP | 0446092 A1 | 9/1991 |
| EP | 0 535 623 A1 | 4/1993 |
| EP | 0553042 A1 | 7/1993 |
| EP | 0565149 A2 | 10/1993 |
| EP | 0 811 357 A1 | 12/1997 |
| FR | 2730155 A1 | 8/1996 |
| GB | 2051581 A | 1/1981 |
| WO | 9514437 A1 | 6/1995 |
| WO | 97/37604 A1 | 10/1997 |
| WO | 9737604 A1 | 10/1997 |
| WO | 99/65415 A1 | 12/1999 |
| WO | 9965415 A1 | 12/1999 |
| WO | 00/19923 A1 | 4/2000 |
| WO | 0019923 A1 | 4/2000 |

OTHER PUBLICATIONS

Oral Argument Requested, US District Court for the Western District of Michigan Northern Division, Defendants' Motion for Summary Judgment That U.S. Patent No. 6,565,565 is Not Invalid.

US District Court for the Western District of Michigan Northern Division, Civil Action No. 2;05 cv 041, Defendants' Reply in Support of Their Motion for Summary Judgment That the '565 Patent is Not Valid.

US District Court for the Western District of Michigan Northern Division, Civil Action No. 2;05 cv 041, Pioneer'S Opposition to Defendants' Motion for Summary Judgment That the '565 Patent is Not Invalid.

* cited by examiner

FIG_9

FIG_10

FIG_12B

FIG_13

FIG_15

FIG_16

DEVICE FOR SECURING SPINAL RODS

CROSS-REFERENCE TO RELATED APPLICATIONS

This application is a continuation of U.S. application Ser. No. 12/827,230, filed Jun. 30, 2012, which is a divisional of U.S. application Ser. No. 10/091,708, filed Mar. 6, 2002, now U.S. Pat. No. 7,780,703, which is a divisional of U.S. application Ser. No. 09/487,942 filed Jan. 19, 2000, now U.S. Pat. No. 6,565,565, which is a continuation-in-part of both U.S. application Ser. No. 09/167,439, filed Oct. 6, 1998, now abandoned, and U.S. application Ser. No. 09/098,927, filed Jun. 17, 1998, now U.S. Pat. No. 6,090,111, the disclosures of which are hereby incorporated by reference herein in their entireties.

BACKGROUND OF THE INVENTION

The subject disclosure relates to implantable spinal stabilization systems for surgical treatment of spinal disorders, and more particularly, to a device for connecting cylindrical spinal rods of a spinal stabilization system to the spine.

The spinal column is a complex system of bones and connective tissue which protects critical elements of the nervous system. Despite these complexities, the spine is a highly flexible structure, capable of a high degree of curvature and twist through a wide range of motion. Trauma or developmental irregularities can result in spinal pathologies which limit this range of motion.

For many years, orthopedic surgeons have attempted to correct spinal irregularities and restore stability to traumatized areas of the spine through immobilization. Over the past ten years, spinal implant systems have been developed to achieve immobilization. Examples of such systems are disclosed in U.S. Pat. Nos. 5,102,412 and 5,181,917 to Rogozinski. Such systems often include spinal instrumentation having connective structures such as elongated rods which are placed on opposite sides of the portion of the spinal column intended to be immobilized. Screws and hooks are commonly utilized to facilitate segmental attachment of such connective structures to the posterior surfaces of the spinal laminae, through the pedicles, and into the vertebral bodies. These components provide the necessary stability both in tension and compression to achieve immobilization.

Various fastening mechanisms have been provided in the prior art to facilitate securement of screws and hooks to the connective structures of a spinal stabilization system. For example, U.S. Pat. No. 5,257,993 to Asher discloses an apparatus for use in retaining a spinal hook on an elongated spinal rod. The apparatus includes a body extending upwardly from a hook portion and having an open ended recess for receiving a spinal rod and an end cap engageable with the body to close the recess. A set screw is disposed in the center of the end cap to clamp the rod in the recess of the body. The end cap and body are interconnectable by different types of connectors including a bayonet connector, a linear cam connector or a threaded connector. Other examples of fastening mechanism for facilitating attachment of screws and hooks to the connective structures of a spinal stabilization system are disclosed in U.S. Pat. No. 5,437,669 to Yuan et al. and U.S. Pat. No. 5,437,670 to Sherman et al.

In each of these prior art examples, threaded fasteners are used to facilitate securement of the connector to the spinal rod. Yet it is well known that threaded fasteners can become loosened under the influence of cyclically applied loads commonly encountered by the spinal column. Furthermore, during assembly, excessive torque applied to a threaded fastener can cause damage to the fastener as well as to the connective device with which it is associated.

It would be beneficial to provide a more reliable and effective mechanism for facilitating the attachment of screws, hooks and clamps to the connective structures of a spinal stabilization system.

BRIEF SUMMARY OF THE INVENTION

The subject disclosure is directed to a device for securing a spinal rod to a fixation device such as a pedicle screw or a lamina hook. The device disclosed herein includes a head portion configured to receive a spinal rod, a locking cap configured to engage the head portion and the spinal rod upon rotation of the locking cap relative to the head portion to secure the position of the head portion relative to the spinal rod, and a fastener portion extending from the head portion and configured to engage the spine. The fastener portion of the device can be in the form of a screw, hook or clamp, or any other configuration known in the art.

The head portion of the device has a channel extending therethrough for receiving a spinal rod and the channel is preferably bounded by opposed side walls each having an arcuate engagement slot defined therein. The locking cap preferably has opposed arcuate engagement flanges configured for reception in the opposed arcuate engagement slots of the head portion upon rotation of the locking cap relative to the head portion. Preferably, the opposed engagement slots are each defined in part by inclined slot surfaces, with the angle of the inclined surface of one engagement slot being opposite that of the opposed engagement slot. Similarly, the opposed engagement flanges are preferably each defined in part by inclined flange surfaces, with the angle of the inclined surface of one engagement flange being opposite that of the opposed engagement flange. The head portion also preferably includes structure for interacting with the locking cap to prevent the opposed side walls of the head portion from expanding radially outwardly when the arcuate flanges are engaged in the arcuate slots.

Preferably, the locking cap of the device is configured for rotation between an initial position in which the arcuate engagement flanges are 90° out of phase with the arcuate engagement slots, an intermediate position in which the arcuate engagement flanges are 45° out of phase with the arcuate engagement slots, and a locked position in which the arcuate engagement flanges are in phase and intimately engaged with the arcuate engagement slots.

In this regard, the bottom surface of the locking cap preferably includes a first recess oriented to accommodate a spinal rod when the locking cap is in an initial unlocked position, a second recesses which intersects the first recess at a first angle to accommodate a spinal rod when the locking cap is in an intermediate position, and a third recess which intersects the elongate recess at a second angle to accommodate a spinal rod when the locking cap is in a final locked position. In accordance with a preferred embodiment of the subject disclosure, the first recess is an elongate recess, the second recess is a transverse recess which intersects the elongate recess at a 45° angle, and the third recess is an orthogonal recess which intersects the elongate recess at a 90° angle.

The subject disclosure is also directed to a device for securing a spinal rod to the spine which comprises a head portion having a channel extending therethrough configured to receive a spinal rod, a locking cap including a first portion configured to engage an interior surface of the head portion and a second portion configured to engage an exterior surface of a spinal rod received by the channel to secure the position of the head portion relative to the spinal rod, and a fastener portion depending from the head portion and configured to engage the spine.

Preferably, the locking cap is a two-piece structure which includes an upper portion configured to engage an interior surface of the head portion and a lower portion configured to engage an exterior surface of the spinal rod to secure the position of the head portion relative to the spinal rod upon rotation of the upper portion relative to the lower portion and the head portion. The upper portion of the locking cap includes a bottom surface having an axial reception bore defined therein and the lower portion of the locking cap includes an upper surface having an axial post extending therefrom configured to engage the axial reception bore in the bottom surface of the upper portion of the locking cap and facilitate the relative rotation of the two parts. The upper portion further includes opposed arcuate engagement flanges configured for cammed engagement in correspondingly configured opposed arcuate engagement slots formed in the opposed side walls of the head portion upon rotation of the upper portion relative to the lower portion. The lower portion further includes a bottom surface having an elongated hemicylindrical recess that is oriented to accommodate a spinal rod extending through the channel in the head portion.

In accordance with one aspect of the subject disclosure, the fastener portion is formed monolithic with the head portion. In accordance with another aspect of the subject disclosure, the fastener portion is mounted for movement relative to the head portion. In this regard, the head portion defines a central axis oriented perpendicular to the spinal rod channel and the fastener portion is mounted for angular movement relative to the central axis of the head portion. More particularly, the fastener portion includes a generally spherical head and a threaded body which depends from the spherical head, and the head portion defines a seat to accommodate the spherical head and an aperture to accommodate the threaded body. In use, upon rotation of the upper portion of the locking cap relative to the lower portion of the locking cap into a locked position, the position of the head portion relative to the spinal rod and the position of the fastener relative to the head portion become fixed.

These and other unique features of the device disclosed herein and the method of installing the same will become more readily apparent from the following description of the drawings.

BRIEF DESCRIPTION OF THE DRAWINGS

So that those having ordinary skill in the art to which the disclosed apparatus appertains will more readily understand how to construct and use the same, reference may be had to the drawings wherein:

FIGS. 6A through 6D illustrate operative steps associated with attaching the bone fastener of the subject disclosure to a spinal rod wherein:

FIGS. 14A through 14C illustrate, in counter-clockwise progression, the operative steps associated with attaching the bone screw of FIG. 11 to a spinal rod by employing the two-piece locking cap of the subject disclosure, wherein:

DETAILED DESCRIPTION

Figures 1, 2:
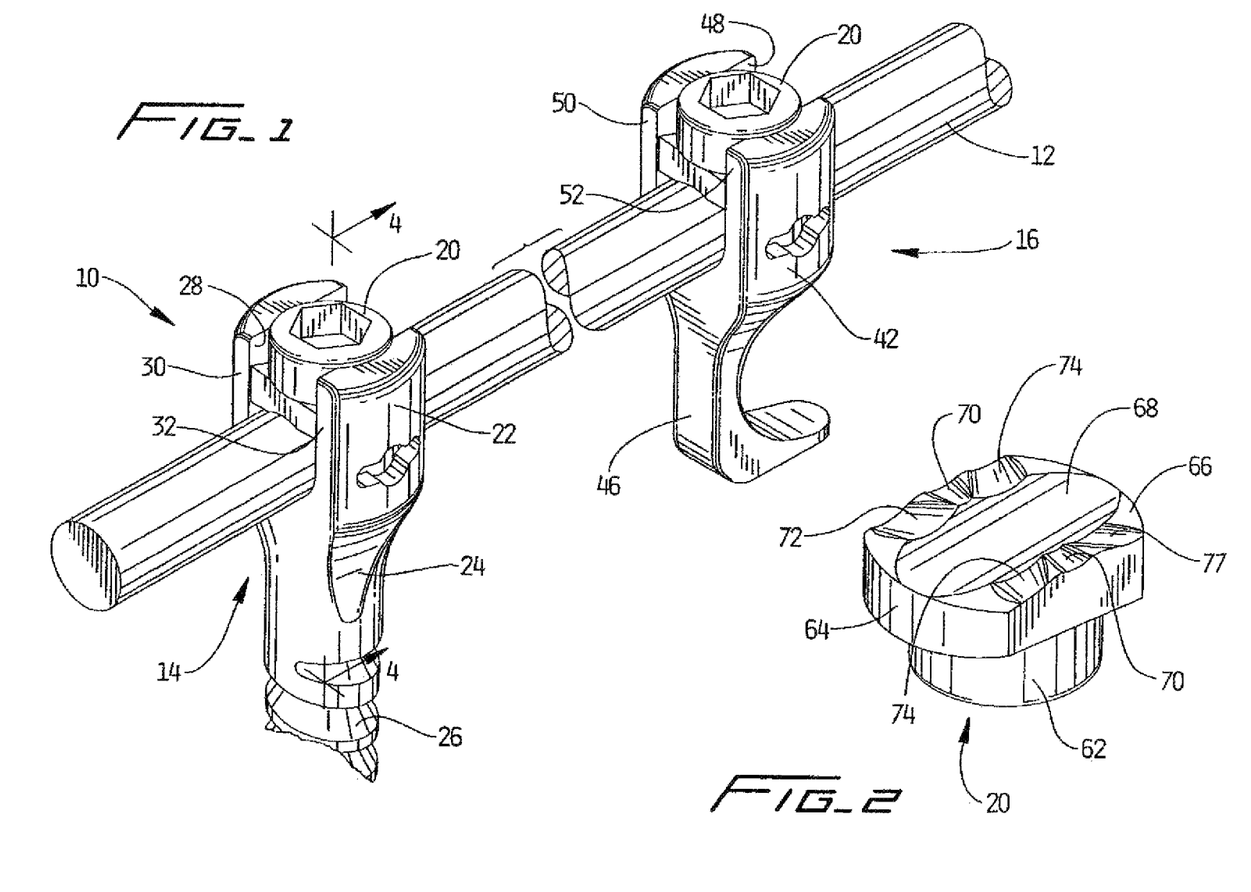
FIG. 1 is a perspective view of an elongated spinal rod of a spinal stabilization system having attached thereto a bone screw and a bone hook constructed in accordance with a first embodiment of the subject disclosure.
FIG. 2 is a perspective view of a locking cap which forms part of the bone screw and bone hook illustrated in FIG. 1, oriented in an inverted position for ease of illustration.

Referring now to the drawings wherein like reference numerals identify similar structural elements of the subject apparatus, there is illustrated in FIG. 1 a section of a spinal stabilization system constructed in accordance with a preferred embodiment of the subject disclosure and designated generally by reference numeral 10.

Referring to FIG. 1, spinal stabilization system 10 includes an elongated spinal rod 12 having a circular cross-section and a substantially smooth outer surface finish. As illustrated, fastening devices in the form of a bone screw 14 and right-angle hook 16 are provided for securing spinal rod 12 to the spine during a spinal stabilization procedure. Both fastening devices employ a novel top-loaded locking cap, designated generally by reference numeral 20, which will be described in greater detail hereinbelow with reference to FIG. 2. The novel locking cap achieves significant clinical advantages over the prior art through its reliability and the ease in which it is installed during a spinal stabilization procedure.

It should be recognized that the subject disclosure is not limited in any way to the illustrated bone screw and right-angle hook. Rather, these particular fasteners are merely examples of the type of devices that can employ the novel locking cap disclosed herein. Other fasteners commonly utilized in spinal stabilization systems, such as, for example, hooks having alternative angular geometries as well as clamps are also envisioned. Indeed, it is envisioned that any component designed for attachment to an elongated spinal rod or transverse coupling rod, may incorporate the novel locking cap of the subject disclosure. Also, any number of fastening devices can be applied along the length of the spinal rod.

Figure 3:
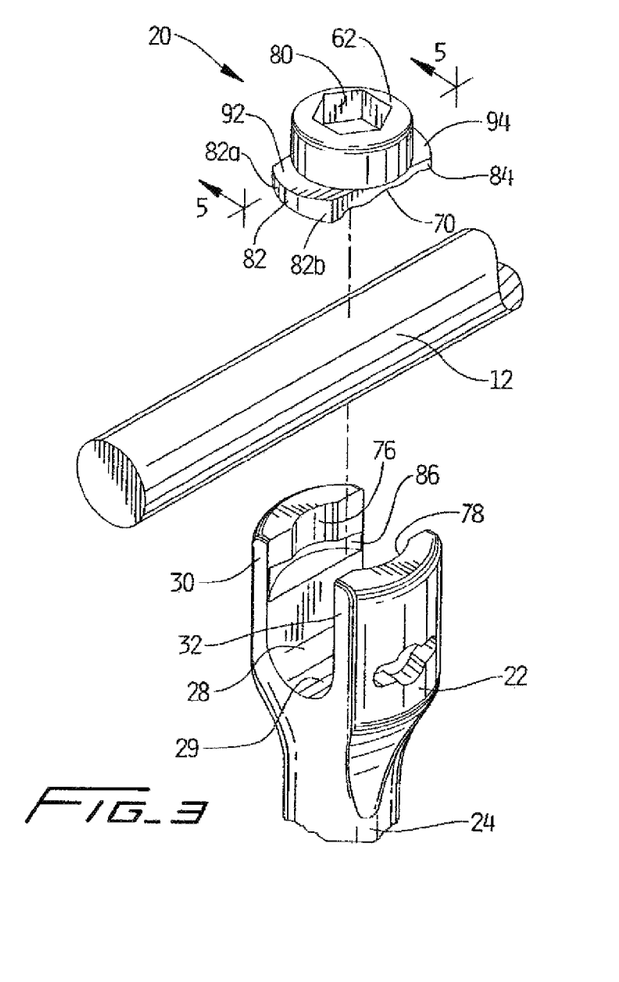
FIG. 3 is a perspective view of the bone screw and locking cap of FIG. 1 separated from one another for ease of illustration.

With continuing reference to FIG. 1. bone screw 14 includes a head portion 22 defining a horizontal axis and a vertical axis. A shank portion 24 depends from the head portion and a threaded portion 26 having a helical thread extending about the outer periphery depends from the shank portion. The helical thread is particularly adapted to securely engage the vertebral bodies of the spine. A channel 28 extends through the head portion 22 along the horizontal axis thereof for receiving elongated spinal rod 12. As best seen in FIG. 3, channel 28 is defined by the interior surfaces of side walls 30 and 32 and the curved lower surface 29 which extends therebetween. Locking cap 20 is dimensioned and configured for reception and engagement in locking channel 28 to secure the position of bone screw 14 with respect to spinal rod 12 during a spinal stabilization procedure.

Referring again to FIG. 1, right-angle hook 16 includes a head portion 42 defining a horizontal axis and a vertical axis. A hook portion 46 depends from the head portion 42 for securement to a vertebral body of the spine. A channel 48 extends through the head portion 42 along the horizontal axis thereof for receiving elongated spinal rod 12. Channel 48 is defined by the interior surfaces of opposed side walls 50 and 52 and a curved lower surface extending therebetween. Locking cap 20 is dimensioned and configured for reception and engagement in channel 48 to secure the position of hook 16 with respect to spinal rod 12 during a spinal stabilization procedure.

Referring now to FIG. 2, there is illustrated locking cap 20 in an inverted position to best illustrate structural aspects thereof. Locking cap 20 includes a cylindrical head 62 and a flanged portion 64. The bottom surface 66 of flanged portion 64 includes an elongate recess having a curvature complementary to spinal rod 12 for accommodating the spinal rod when locking cap 20 is in an unlocked position, shown for example in FIG. 6B. In such a position, the fastening device may be moved freely along or rotated about the longitudinal axis of the spinal rod. Bottom surface 66 also includes a bifurcated orthogonal recess 70 which intersects the elongate recess at a 90° angle and has a curvature complementary to spinal rod 12 to accommodate the spinal rod when locking cap 20 is in a locked position, shown for example in FIG. 6D and FIG. 4. In addition, bottom surface 66 includes bifurcated first and second transverse recesses 72 and 74 which intersect the elongate recess 68 at opposite angles of intersection and have curvatures which are complementary to spinal rod 12 to accommodate the spinal rod when the locking cap 20 is in either of two intermediate positions, one of which is shown for example in FIG. 6C. In such a position, the fastening device retains the spinal rod but is not fully secured, and if desired by the surgeon, locking cap 20 can be rotated from the intermediate position and the fastener moved to an alternative location on the spinal rod. Preferably, the transverse recesses intersect the elongate recess at opposed 45° angles. However, those skilled in the art will readily appreciate that the transverse recess can be oriented at alternative intersecting angles. It is also contemplated that the bottom surface can be flat without any recesses.

Figure 5:
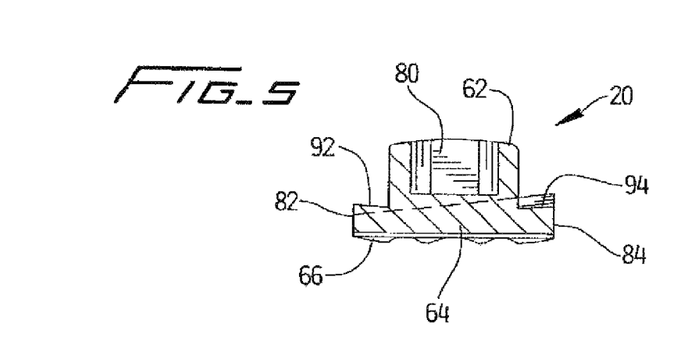
FIG. 5 is a cross-sectional view of the locking cap taken along line 5-5 of FIG. 3.

Referring to FIGS. 3 and 5, the cylindrical head 62 of locking cap 20 includes a hexagonal axial bore 80 extending partially therethrough for receiving a working implement such as a wrench to facilitate rotation of the locking cap 20 relative to the head portion 22 of the fastening device about the vertical axis defined thereby. It envisioned that alternative tooling configurations known in the art can also be utilized to facilitate axial rotation of locking cap 20 during a surgical procedure. Curved notches 76 and 78 are formed in the inner surfaces of opposed walls 30 and 32 for accommodating the cylindrical head 62 of locking cap 20 when the locking cap is received and rotated within channel 28.

The flanged portion 64 of locking cap 20 is defined in part by two diametrically opposed arcuate engagement flanges 82 and 84 which are dimensioned and configured for operative engagement with two complementary diametrically opposed arcuate engagement slots 86 and 88 defined in the interior surfaces of the opposed side walls 30 and 32 of head portion 22. (See FIG. 4).

Figure 4:
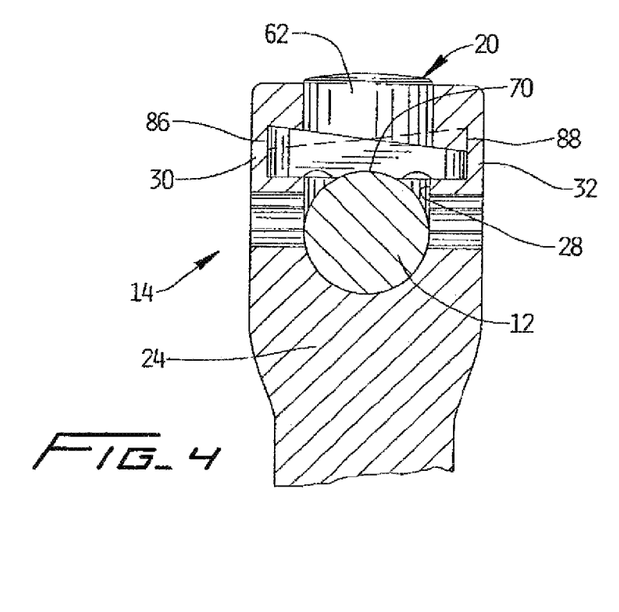
FIG. 4 is a cross-sectional view of the bone screw of the subject disclosure taken along line 4-4 of FIG. 1.

With continuing reference to FIGS. 3 through 5, engagement flanges 82 and 84 define ramped camming surfaces 92 and 94, respectively. Camming surfaces 92 and 94 are of opposite angular inclination with respect to one another. More particularly, each engagement flange has a low side (e.g., 82a of flange 82) and a high side (e.g., 82b of flange 82), whereby the low sides of the two flanges are diametrically opposed from one another as are the high sides. Actually, the camming surfaces of the flanges are mirror images of one another. Thus, the locking cap can be initially oriented with either flange aligned to engage either slot. This versatility adds to the ease in which the locking cap is installed during a surgical procedure.

As best seen in FIG. 4, the arcuate engagement slots 86 and 88 in head portion 22 of fastener 14 have inclined surfaces which mate with the ramped camming surfaces 92 and 94 of flanges 82 and 84. As best seen in FIG. 5, the ramped camming surfaces 92 and 94 are tapered radially inwardly to enhance the interlock with the mating surfaces of arcuate engagement slots 86 and 88, which are also tapered to complement the radially inward taper of camming surfaces 92 and 94. This interlocking relationship serves to prevent the opposed side walls 30 and 32 of head portion 22 from spreading radially outward as the arcuate flanges are engaged with the arcuate slots when the locking cap 20 is rotated to a locked position.

Figure 6A:
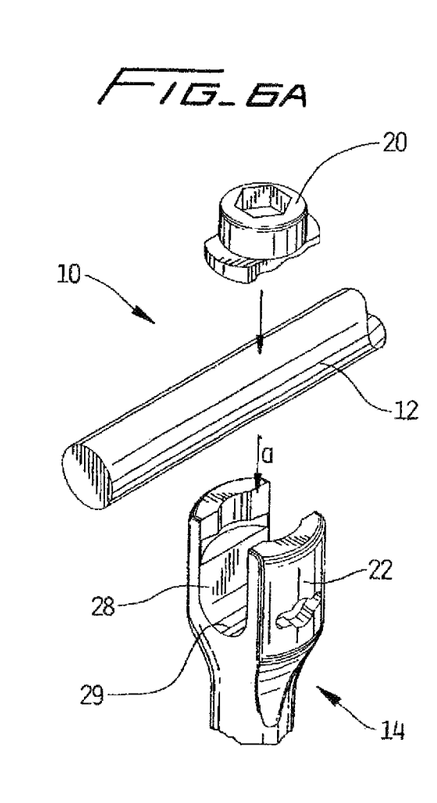
FIG. 6A illustrates the step of positioning the spinal rod and locking cap in the reception channel of the head portion of a fastening device of the subject disclosure.

FIGS. 6A through 6D illustrate the steps in securing the fastening device to the spinal rod during a surgical procedure. Although attachment of a bone screw 14 is shown, it should be understood, as noted above, that other fastening devices, e.g., bone hooks, can be secured to the spinal rod 12 using the locking cap and head portion structure of the present disclosure. Initially, as illustrated in FIG. 6A, spinal rod 12 is moved into approximation with the horizontal channel 28 of head portion 22 such that the periphery of the spinal rod 12 is in registration with the curved surface 29 of the channel 28. Locking cap 20 is then top loaded into the channel along the vertical axis of the fastener in the direction of arrow a. At such a time, spinal rod 12 is accommodated within the elongate recess 68 defined in the bottom surface 66 of locking cap 20 and the bone screw 14 may be moved freely relative to the spinal rod. The opposed flanged sections 82 and 84 of locking cap 20 are 900 out of phase from the opposed arcuate engagement slots 86 and 88 defined in head portion 22, as shown for example in FIG. 6B.

Figures 6B, 6C, 6D:
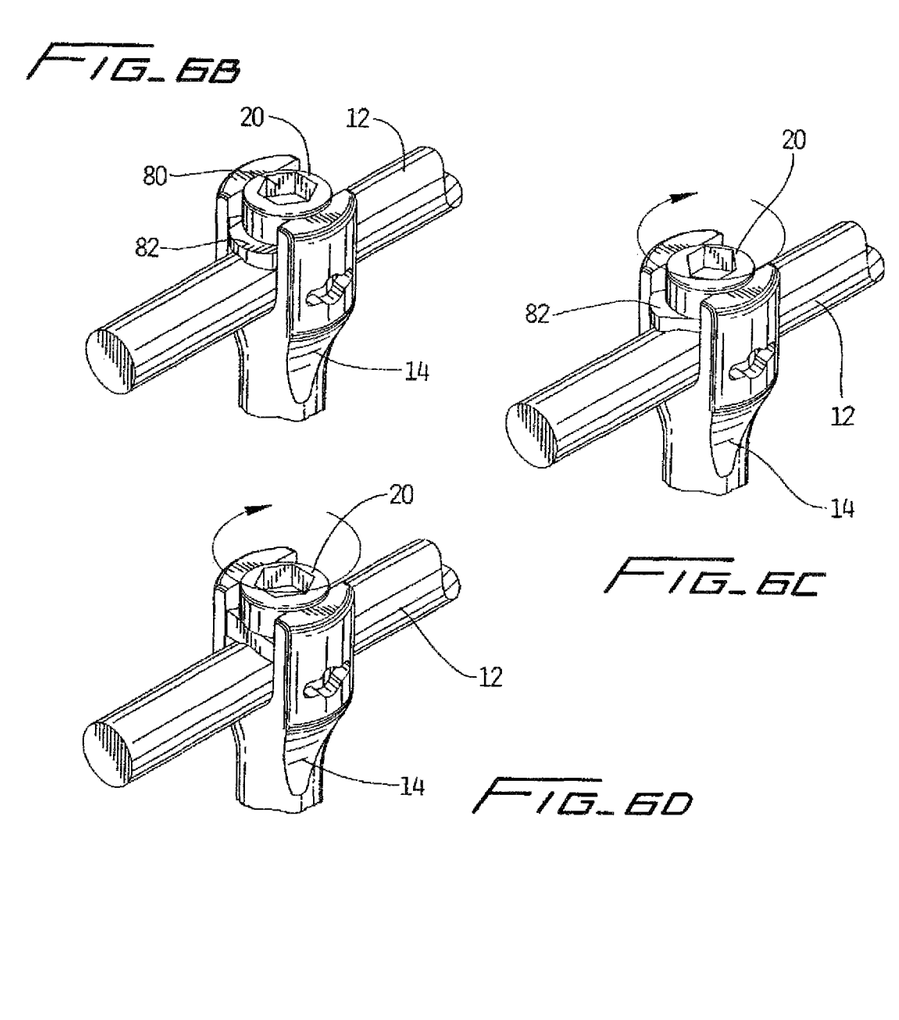
FIG. 6B illustrates the initial orientation of the locking cap relative to the head portion of a fastening device of the subject disclosure wherein the locking cap is in an unlocked position.
FIG. 6C illustrates the rotation of the locking cap relative to the head portion of a fastening device of the subject disclosure to a partially locked position.
FIG. 6D illustrates the rotation of the locking cap relative to the head portion of a fastening device of the subject disclosure to a locked position.

Thereafter, as shown in FIG. 6C, locking cap 20 is rotated 45° relative to head portion 22 about the vertical axis thereof. At such a time, spinal rod 12 is accommodated within one of the two transverse recesses 72 or 74, depending upon the initial orientation of the locking cap 20 with respect to the head portion. Thereupon, the opposed arcuate engagement flanges 82 and 84 of locking cap 20 are only partially engaged with the opposed arcuate engagement slots 86 and 88 defined in head portion 22, as they are 45° out of phase with the slots. Consequently, the locking cap holds the fastener 22 and spinal rod 12 together, but does not lock the fastener. In this position, the locking cap 20 can be readily rotated in the opposite direction to disengage from the spinal rod 12 to adjust the position of the bone screw 14 with respect to the spinal rod 12.

Once the desired position and orientation of the bone screw 14 has been attained, locking cap 20 is rotated another 45° to the locked position illustrated in FIG. 6D. At such a time, spinal rod 12 is accommodated within the orthogonal recess 70 defined in the bottom surface of locking cap 20. Thereupon, the opposed engagement flanges 82 and 84 of flanged portion 64 are fully engaged with the opposed engagement slots 86 and 88 of head portion 22 and the longitudinal and angular orientations of the bone screw 14 are fixed with respect to spinal rod 12, as illustrated in FIG. 4. It should be readily apparent that the manner and method by which bone screw 14 hook is attached to spinal rod 12 is identical to the manner and method by which hook 16 or other fasteners are attached to spinal rod 12.

Since the rotational range of locking cap 20 is limited, i.e., the locking cap can only be rotated 90°, it will be readily appreciated that the cap cannot be over-torqued. Thus, the damage often caused by over-tightening a conventional threaded locking mechanism, such as a set screw, is avoided. Furthermore, since the locking cap of the subject disclosure has a predetermined locked position, it is unlikely that it will be under-torqued or left in a loose condition after installation as is common with threaded set screws found in the prior art. That is, by having a predetermined locked position, uniform locking forces are provided for all of the fastening devices used to secure the spinal rod 12 along its length and cross threading is reduced.

Figure 7:
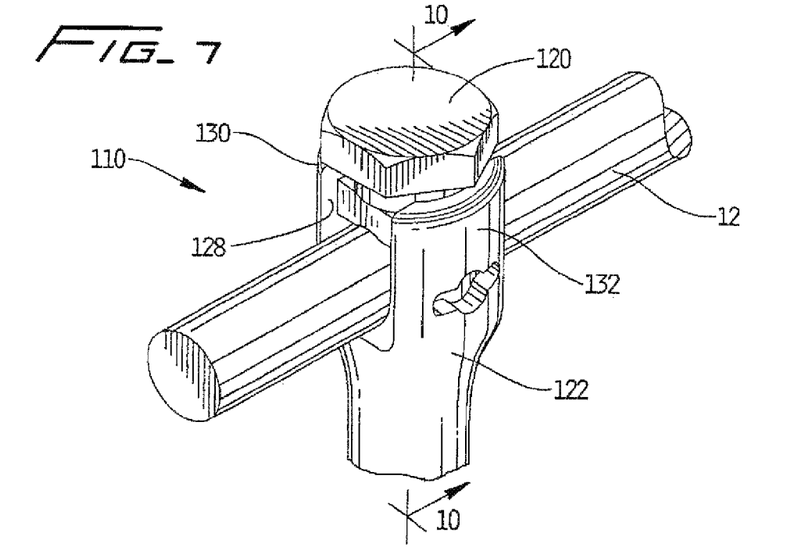
FIG. 7 is a perspective view of a fastening device constructed in accordance with a second embodiment of the subject disclosure.
Figure 8:
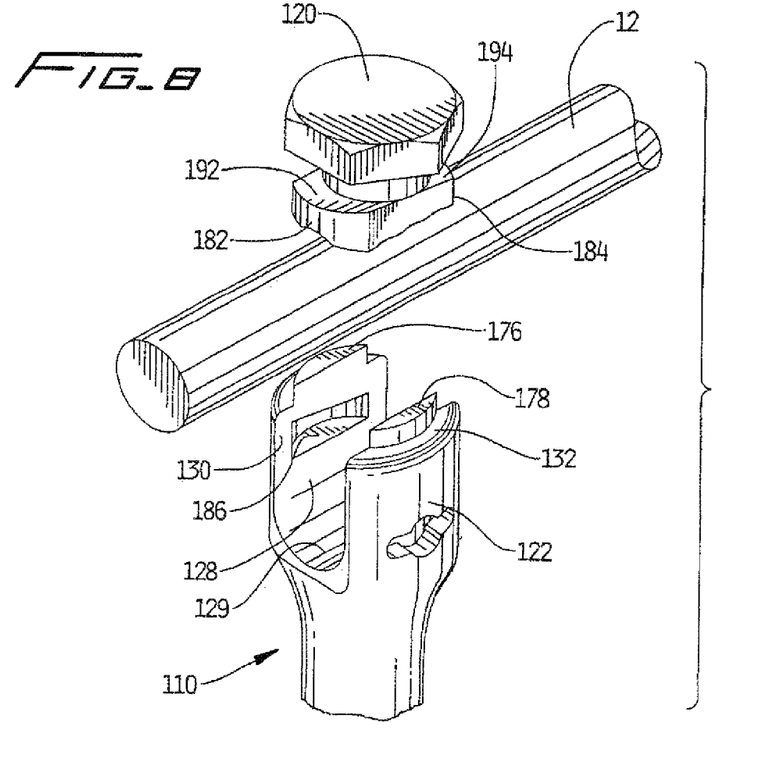
FIG. 8 is a perspective view of the fastening device of FIG. 7 with the locking cap separated for ease of illustration.

Referring now to FIGS. 7 and 8, there is illustrated another fastening device constructed in accordance with a preferred embodiment of the subject disclosure and designated generally by reference numeral 110. Fastening device 110 is similar to fastening devices 12 and 14 in that it is particularly designed to facilitate securement of a spinal rod to the spine in a convenient manner. Fastening device 110 includes a head portion 122 having opposed side walls 130 and 132 which define a horizontal channel 128 in conjunction with the curved lower surface 129 extending therebetween. Arcuate tabs 176 and 178 project upwardly from side walls 130 and 132, respectively, for interacting with locking cap, 120.

Figure 9:
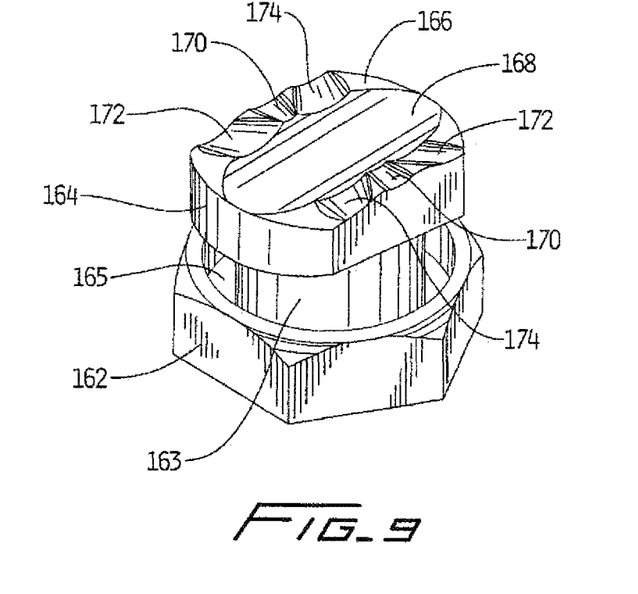
FIG. 9 is a perspective view of the locking cap of the fastener device of FIG. 7, oriented in an inverted position for ease of illustration.

Referring to FIG. 9, locking cap 120, which is shown in an inverted position for ease of illustration, includes a hexagonal head 162 a cylindrical body 163 and a flanged portion 164. The hexagonal head 162 is adapted and configured for interaction with a wrench or similar work implement. An annular channel 165 extends into the bottom surface of hexagonal head 162 for receiving arcuate tabs 176 and 168 This positive interaction serves to prevent the opposed side walls 130 and 132 of head portion 122 from spreading radially outwardly when arcuate flanges 182 and 184 of locking cap 120 are engaged in arcuate slots 186 and 188 of head portion 122 upon rotation of locking cap 20 into a locked position. Thus, in this embodiment, the ramped camming surfaces 192 and 194 of the arcuate engagement flanges 182 and 184 need not be provided with radially inwardly directed tapers as provided on flanges 82 and 84 of the locking cap 20 of the embodiment of FIGS. 1-6.

Figure 10:
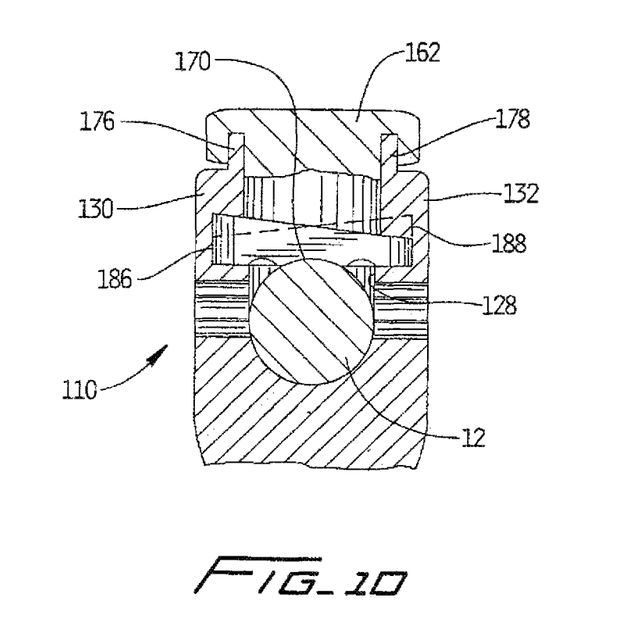
FIG. 10 is a cross-sectional view of the fastening device of FIG. 7 taken along line 10-10 of FIG. 7.

With continuing reference to FIG. 9, the bottom surface 166 of the flanged portion 164 of locking cap 120 is configured in substantially the same manner as the bottom surface 66 of locking cap 20 in that it is provided with an elongate recess 168 for accommodating a spinal rod when the locking cap 120 is in an unlocked position, first and second bifurcated transverse recesses 172 and 174 which intersect the elongate recess 168 at opposite 45° angles to accommodate the spinal rod when the locking cap 120 is in either of two intermediate positions, and a bifurcated orthogonal recess 170 which intersects the elongate recess at a 90° angle to accommodate the spinal rod when the locking cap 120 is in a final locked position, as shown in FIG. 10. It will be readily appreciated that locking cap 120 is engaged with fastening device 110 in a manner that is substantially similar to the manner in which locking cap 20 is engaged with bone fastener and hook 16, and that the configuration of the bottom surface of flanged portion 164 provides the same benefits afforded by the flanged portion 64 of locking cap 20.

Figure 11:
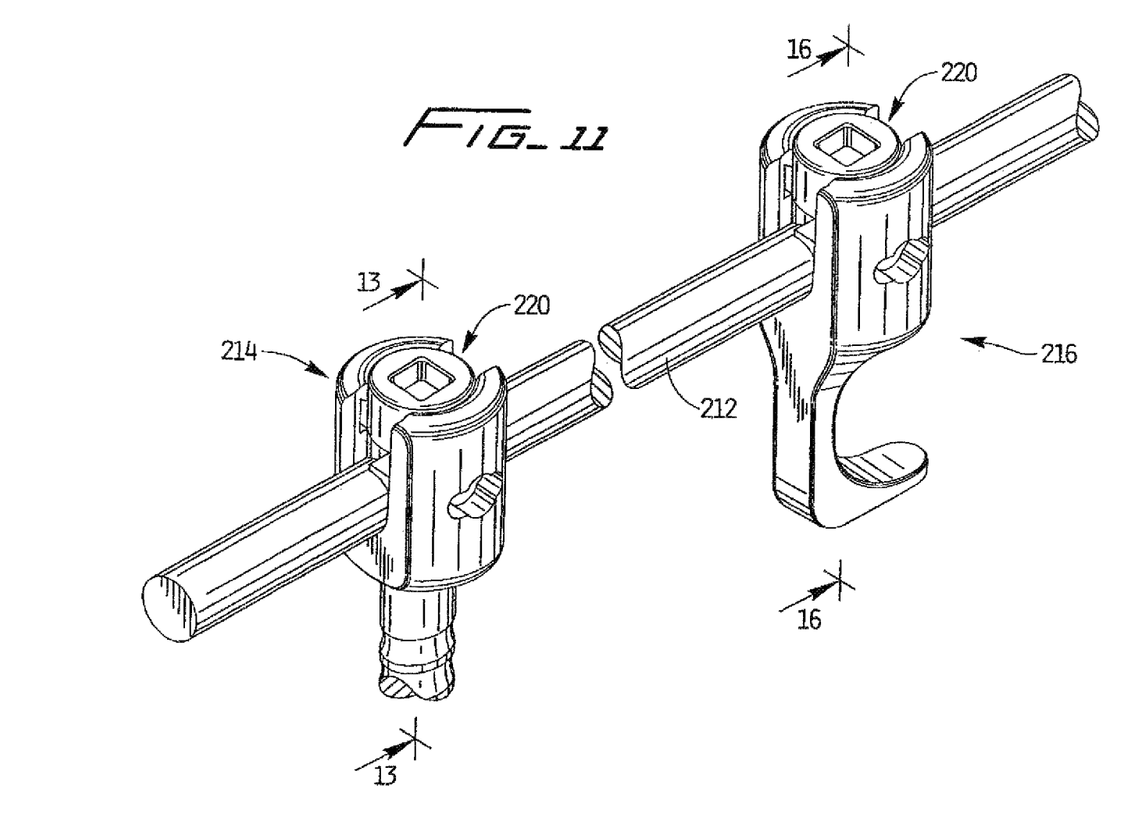
FIG. 11 is a perspective view of an elongated spinal rod of a spinal stabilization system having attached thereto another version of a bone screw and another version of a bone hook constructed in accordance with another embodiment of the subject disclosure.

Referring now to FIG. 11, there is illustrated two additional fastening devices constructed in accordance with the subject disclosure in the form of a multi-axial bone screw 214 and a right-angle hook 216 which are provided for securing spinal rod 212 to the spine during a spinal stabilization procedure. Both fastening devices employ a novel top loaded two-piece locking cap, designated generally by reference numeral 220, which will be described in greater detail hereinbelow with reference to FIGS. 12 and 13. The novel two-piece locking cap achieves significant clinical advantages over the prior art through its reliability and the ease in which it is installed during a spinal stabilization procedure. As with respect to the previously described embodiments of FIG. 1, the novel two-piece locking cap may be used in conjunction with other types of fasteners commonly employed in spinal stabilization procedures. Moreover, while the two-piece locking cap illustrated in FIG. 11 is employed with a multi-axial bone screw, it is readily apparent that the same two-piece locking cap could be employed with a fixed axis bone screw such as that which is illustrated in FIG. 1.

Figure 12A:
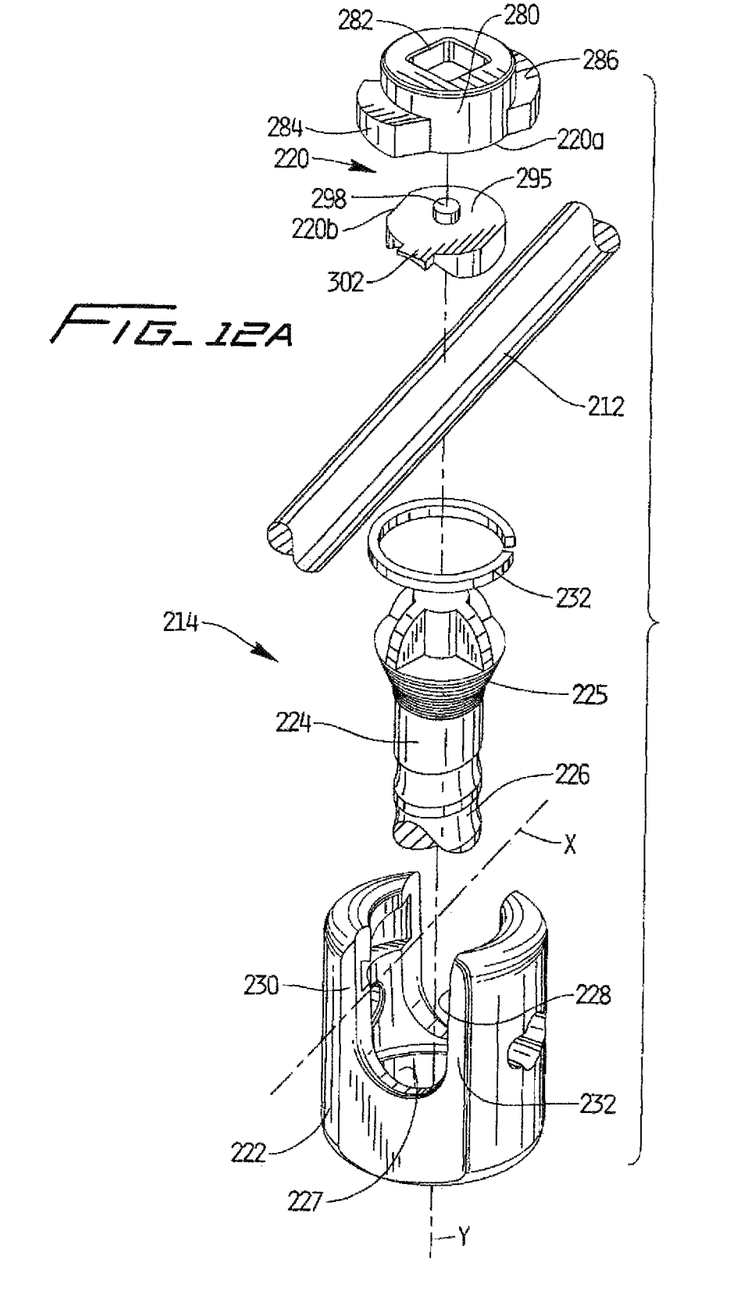
FIG. 12A is an exploded perspective view of the bone screw of FIG. 11 with parts separated for ease of illustration including the two-piece locking cap and multi-axial fastener portion associated therewith.
Figure 13:
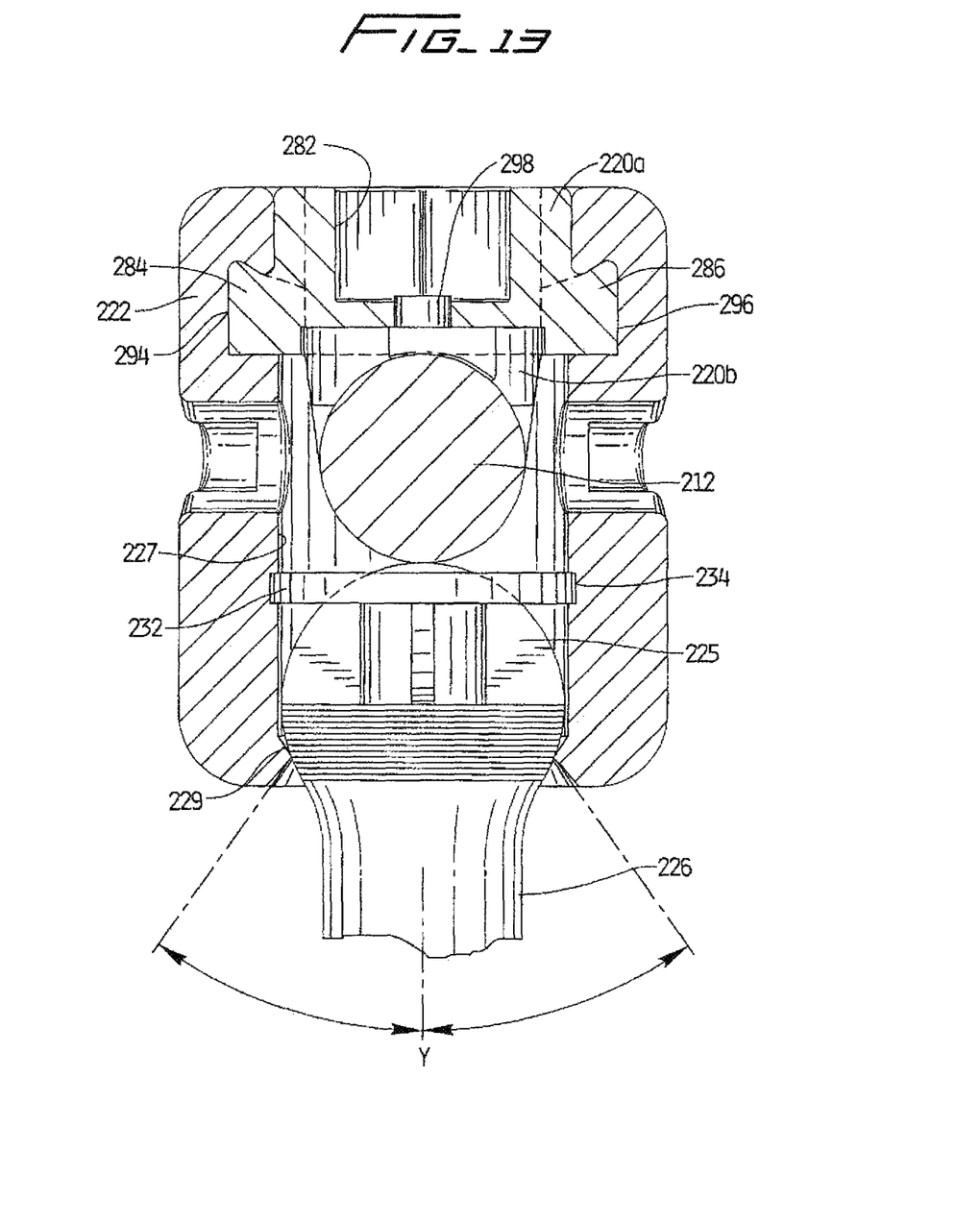
FIG. 13 is a cross-sectional view of the bone screw of FIG. 11 taken along line 13-13 of FIG. 11 with the two-piece locking cap in a locked position.

Referring to FIGS. 12A and 13, the multi-axial bone screw 214 includes a head portion 222 defining a horizontal axis "x"

and a vertical axis "y". A channel 228 extends through the head portion 222 along the horizontal axis "x" for receiving an elongated spinal rod 212. Channel 228 is defined by the interior surfaces of the side walls 230 and 232 of head portion 222. Bone screw 214 further includes a fastener portion 224 which includes a generally spherical head 225 and a threaded body 226. Threaded body 226 depends from and is monolithically formed with the spherical head 225. The threaded body includes a helical thread formation that is particularly adapted to securely engage the vertebral bodies of the spine.

The head portion 222 of multi-axial bone screw 214 further defines a generally cylindrical vertical channel 227 which extends through and is aligned with the vertical axis "y" of the head portion 222. Vertical channel 227 is configured to receive and accommodate the fastener portion 224 of bone screw 214. More particularly, as best seen in FIG. 13, a lower interior surface portion of vertical channel 227 defines an annular seating surface 229 configured to cooperate with the lower hemi-spherical region of spherical head 225. The cooperative engagement between the two structures permits the relative movement of the fastener portion 224 with respect to the head portion 222 about the vertical axis y. The multi-axial motion afforded thereto, enhances the operational range of bone screw 214, providing greater flexibility to the surgeon during a spinal stabilization procedure.

Bone screw 214 further includes an annular retention ring 232 that is accommodated within a corresponding annular groove 234 formed within the cylindrical wall of vertical channel 227 (see FIG. 13). Retention ring 232 is adapted to positively engage the spherical head 225 and aiding in its stabilization. In addition, as best seen in FIG. 13, the lower hemi-spherical region of head 225 is scored with a series of circular ridges adapted to enhance the frictional coefficient of the seating surface defined thereby.

Referring to FIG. 12A, bone screw 214 further includes a two-piece locking cap 220 which is dimensioned and configured for reception and engagement in the horizontal channel 228 of head portion 220 to secure the position of head portion 222 with respect to spinal rod 212 during a spinal stabilization procedure. In addition, as described in detail hereinbelow with respect to FIG. 13, the securement of locking cap 220 within channel 228 also achieves positive fixation of the angular position of the fastener portion 224 with respect to the head portion 222 and the vertical axis "y" defined thereby.

Figure 12B:
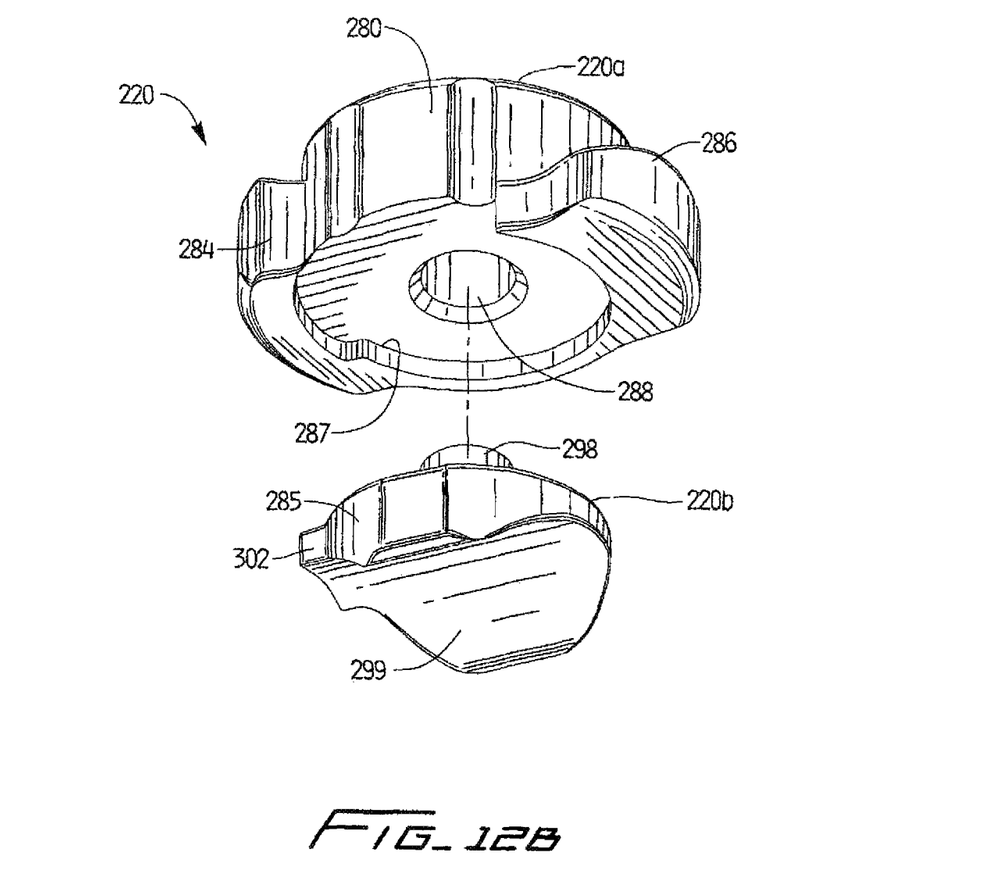
FIG. 12B is a perspective view, looking upward from below, of the two-piece locking cap of the subject disclosure illustrating the bottom surface features of the component parts thereof.

As illustrated in FIGS. 12A and 12B, locking cap 220 includes an upper portion 220a and a lower portion 220b. The upper portion 220a includes a cylindrical cap body 280 defining an axial reception port 282 for receiving a tool or working implement that applies torque to the cap during installation. Upper portion 220a further includes a pair of circumferentially opposed arcuate engagement flanges 284 and 286 which extend radially outwardly from cap body 280. Engagement flanges 284 and 286 include inclined radially inwardly slopping camming surfaces for cooperating with complementary opposed arcuate engagement slots 294 and 296 formed in the opposed side walls 230 and 232 of head portion 222 (see FIG. 13). As described in more detail hereinbelow with respect to FIGS. 14a-14d, the flanges 284, 286 become engaged in corresponding slots 294, 296 upon rotation of the upper portion 220a of locking cap 220 relative to the head portion 222 of bone screw 214.

The lower portion 220b of locking cap 220 is configured for cooperative reception within the cylindrical vertical channel 227 of head portion 222 and is adapted to engage the spinal rod 212 extending through the horizontal channel 228 of head portion 222. More particularly, the body 285 of the lower portion 220b has curved exterior surfaces which complement the curvature of the walls defining vertical channel 227. Thus, when the locking cap 220 is loaded into vertical channel 227, a positive mating relationship is achieved between the lower portion 220b of locking cap 220 and vertical channel 227. As a result, the axial position of lower portion 220b becomes fixed with respect to head portion 222 and spinal rod 212. Furthermore, as best seen in FIG. 12B, a hemi-cylindrical channel 299 is formed in the undersurface of lower portion 220b for intimately cooperating with the cylindrical spinal rod 212 upon loading the locking cap 220 in vertical channel 227. Body portion 285 includes an extension flange 302 which aides in the alignment and positioning of the lower cap portion 220a with respect to spinal rod 212.

As best seen in FIG. 12B, the bottom surface of the upper portion 220a of locking cap 220 includes a recessed seating area 287 and an associated axial reception bore 288. The recessed seating area 287 is dimensioned and configured to accommodate the body of the lower portion 220b of locking cap 220, while the reception bore 288 is dimensioned and configured to receive and engage an axial post 298 which projects from the upper surface 295 of the lower portion 220b of locking cap 220. More particularly, during assembly, when the axial post 298 is received by the reception bore 288, the top end of the post is swaged (flared out) to join the two components together (see FIG. 13). The interaction of the axial post 298 and axial reception bore 288 facilitates relative rotational movement of the upper portion 220a relative to the lower portion 220b when the locking cap 220 is loaded into and locked in the head portion 222 of bone screw 214 during a spinal stabilization procedure.

As described in detail hereinbelow with reference to FIGS. 14A-14C, the two-part locking cap enables a surgeon to load the locking cap 220 into vertical channel 227 and properly position the lower portion 220b against the spinal rod 212 so as to ensure an intimate engagement between the hemi-cylindrical channel 299 and the cylindrical surface of the spinal rod. Thereafter, the upper portion 220a may be rotated into a locked portion relative to the lower portion 220b.

Figure 14A:
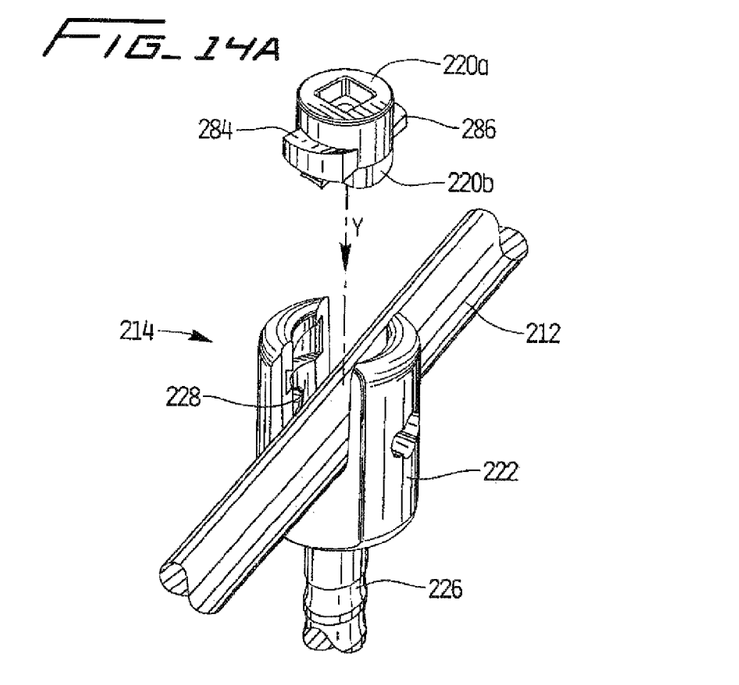
FIG. 14A illustrates the step of positioning the locking cap within the head portion of the bone screw.
Figure 14B:
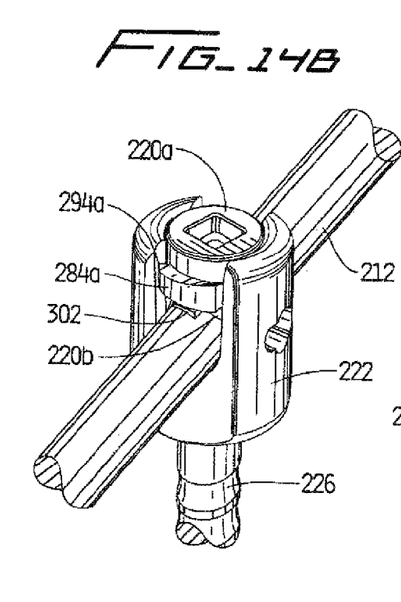
FIG. 14B illustrates the initial unlocked orientation of the upper portion of the locking cap within the head portion of the bone screw.
Figure 14C:
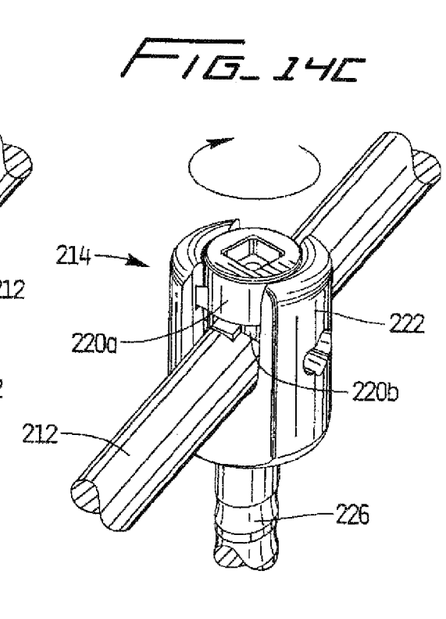
FIG. 14C illustrates the step of rotating the upper portion of the locking cap relative to the lower portion of the locking cap and the head portion of the bone screw into a locked position to secure the position of the bone screw with respect to the spinal rod.

Referring now in detail to FIGS. 14A-14C, during a spinal stabilization procedure, the fastener portion 226 of bone screw 214 is first seated within the head portion 222. Then, the head portion 222 is positioned at the surgical site in such a manner so that the elongated spinal rod 212 extends through the horizontal channel 228 as illustrated in FIG. 14A. Thereafter, if necessary, the fastener portion 226 may be moved into a desired angular orientation by the surgeon and subsequently mounted to the spinous process using suitable surgical instruments.

With reference to FIG. 14B, once the appropriate position of the fastener portion 226 has been established by the surgeon, the locking cap 220 is loaded into the vertical channel 227 of head portion 222 along the vertical axis "y" defined thereby. At such a time, the hemi-cylindrical channel 299 on the undersurface of lower portion 220b will become intimately engaged with the cylindrical surface of the spinal rod 212 and it will be maintained in a fixed axial orientation with respect to the spinal rod due to the mating relationship between the body of the lower portion 220b and the vertical channel 227.

Locking cap 220 must be loaded in such a manner so that the radially outwardly extending engagement flanges 284 and 286 of upper portion 220a are parallel to the axis of the spinal rod 212, as illustrated in FIG. 14B. Otherwise, the flanges will interfere with the opposed side walls 230 and 232 of the head portion 222. Furthermore, care must be taken to ensure that the upper portion 220a of locking cap 220 is positioned in such a manner so that the low sides of the flanges (e.g. 284a)

are aligned with the high sides of the engagement channels (e.g. 294*a*), or the flanges will not cammingly engage the channels upon rotation of the upper portion 220*a* of the locking cap 220 relative to the head portion 222 of bone screw 214.

Once the upper portion 220*a* of locking cap 220 has been properly oriented with respect to head portion 222 with the extension flange 302 in alignment with spinal rod 212, it is rotated in a clockwise direction about the vertical axis "y" relative to the lower portion 220*b* of locking cap 220 and the head portion 222 of bone screw 214 using an appropriate surgical implement or tool (not shown). Thereupon, the arcuate engagement flanges 284, 286 of upper portion 220 cammingly engage the corresponding engagement slots 284. Once rotated into a locked portion, the lower portion 220*b* of the locking cap 220 will be seated within the recessed seating area 287 defined in the bottom surface 285 of the upper portion 220*a* of locking cap 220 (See FIG. 13). At such a time, the position of the head portion 222 of bone screw 214 is fixed with respect to longitudinal axis of spinal rod 212 and the position of the fastener portion 226 of bone screw 214 is fixed with respect to the vertical axis "y" defined by head portion 222 of bone screw 214, as illustrated in FIG. 14C.

Figure 15:
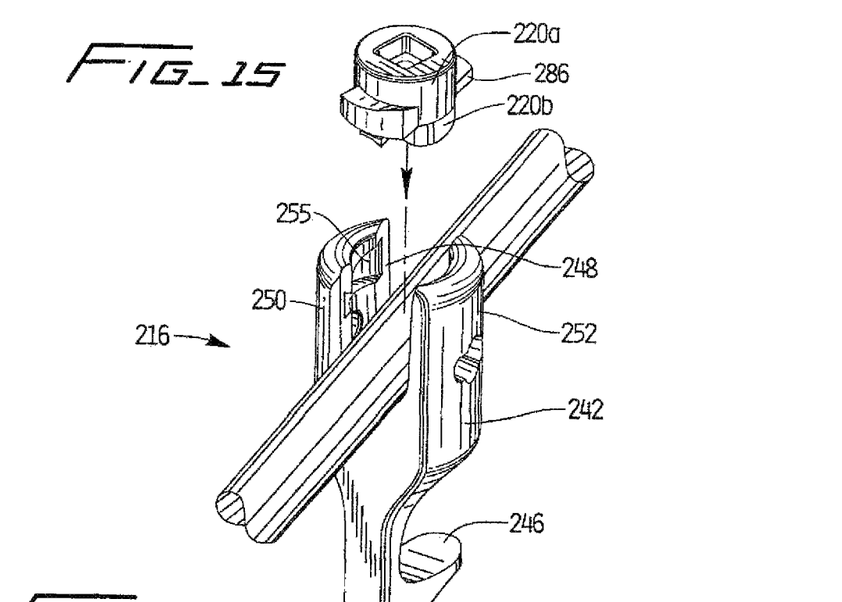
FIG. 15 is an exploded perspective view of the bone hook of FIG. 11 with parts separated for ease of illustration including the two-piece locking cap associated therewith.
Figure 16:
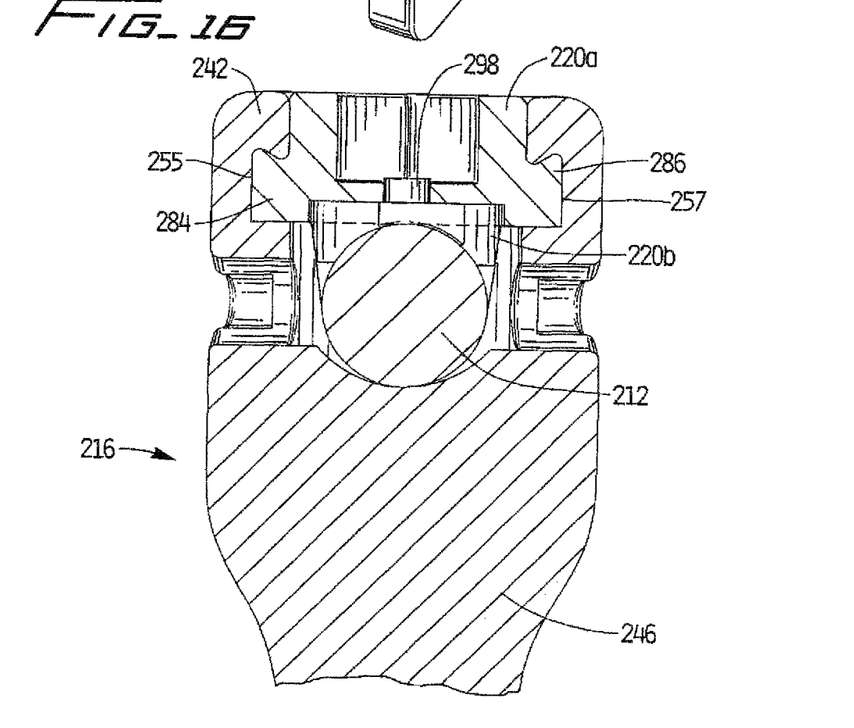
FIG. 16 is a cross-sectional view of the bone hook of FIG. 11 taken along line 16-16 of FIG. 11 with the two-piece locking cap in a locked positions These and other features of the apparatus disclosed herein will become more readily apparent to those having ordinary skill in the art from the following detailed description of the preferred embodiments taken in conjunction with the drawings.

Referring now to FIGS. 15 and 16, the right-angle hook 216 of the subject disclosure includes a head portion 242 defining a horizontal axis x and a vertical axis "y". A hook portion 246 depends from the head portion 242 to facilitate securement of the device to a vertebral body of the spine. A channel 248 extends through the head portion 242 along the horizontal axis thereof for receiving elongated spinal rod 212. Channel 248 is defined by the interior surfaces of opposed upstanding side walls 250 and 252 and a contoured lower surface extending therebetween for complementing the shape of the rod. Channel 248 is further configured to receive a two-piece locking cap 220 adapted to secure the position of hook 216 with respect to spinal rod 212 during a spinal stabilization procedure.

As discussed hereinabove with respect to multi-axial bone screw 214, the locking cap 220 includes an upper portion 220*a* and a lower portion 220*b* which are rotatably joined together. The upper portion includes a pair of circumferentially opposed arcuate engagement flanges 284 and 286 for cooperating with complementary opposed arcuate engagement slots 255 and 257 formed in the opposed side walls 250 and 252 of head portion 242. As described in more hereinabove with respect-to FIGS. 14A-14C, the flanges 284, 286 become engaged in corresponding slots 255, 257 upon rotation of the upper portion 220*a* of locking cap 220 relative to the lower portion 220*b* of the locking cap and the head portion 242 of right-angle hook 216.

Although the apparatus disclosed herein has been described with respect to preferred embodiments, it is apparent that modifications and changes can be made thereto without departing from the spirit and scope of the invention as defined by the claims.

The invention claimed is:

1. A device for securing a spinal rod to the spine comprising:
    a) a head portion having a channel configured to receive a spinal rod and a set of spaced apart slots;
    b) a fastener portion depending from the head portion and being configured to engage bone; and
    c) a locking cap having a first portion with flanges extending outward from a body of the first portion, and a second portion rotatably coupled to the first portion, the second portion including a bottom surface with an elongate recess extending along an axis and being adapted to engage the spinal rod, wherein rotation of the first portion of the locking cap with respect to the second portion forces at least one of the flanges against at least one of the slots in the head portion in a direction transverse to the axis to secure the spinal rod relative to the head portion.

2. The device of claim 1, wherein the first and second portions of the locking cap are rotatably coupled via a projection extending from the second portion.

3. The device of claim 2, wherein the projection is an axial post, and the first portion of the locking cap includes an opening for receiving the axial post.

4. The device of claim 3, wherein the axial post extends from the second portion of the locking cap in a direction extending transverse to the axis of the recess.

5. The device of claim 3, wherein a portion of the axial post flares outward when inserted into the opening in the first portion of the locking cap to join the first and second portions of the locking cap together.

6. The device of claim 1, wherein the flanges of the first portion of the locking cap cammingly engage the spaced apart slots of the head portion upon rotation of the first portion of the locking cap with respect to the second portion.

7. The device of claim 1, wherein the second portion of the locking cap is rotatably engaged with a bottom surface of the first portion.

8. The device of claim 1, wherein rotation of the first portion of the locking cap with respect to the second portion cammingly forces at least one of the flanges against at least one of the slots in the head portion.

9. A device for securing a spinal rod to the spine comprising:
    a) a head portion having a first and second side walls defining a channel configured to receive a spinal rod, the head portion including a set of spaced apart slots;
    b) a fastener portion depending from the head portion and being configured to engage bone; and
    c) a locking cap having a first portion with flanges extending outward from a body of the first portion, and a second portion rotatably coupled to the first portion, the second portion including a projection and a bottom surface with an elongate recess, wherein rotation of the first portion of the locking cap with respect to the second portion forces at least one of the flanges against at least one of the slots in the head portion to secure the spinal rod relative to the head portion, and wherein the elongate recess is configured to engage the spinal rod.

10. The device of claim 9, wherein the projection is an axial post extending in a direction transverse to an axis of the elongate recess.

11. The device of claim 10, wherein the first portion of the locking cap includes an opening for receiving the axial post, and the first portion of the locking cap is rotatable with respect to the second portion about the axial post once it is inserted into the opening.

12. The device of claim 11, wherein a portion of the axial post flares outward when inserted into the opening in the first portion of the locking cap to join the first and second portions of the locking cap together.

13. The device of claim 9, wherein the second portion of the locking cap is rotatably engaged with a bottom surface of the first portion.

14. The device of claim 9, wherein the fastener and head portions each extend along respective longitudinal axes, the longitudinal axis of the fastener portion being arrangeable at multiple different angles relative to the longitudinal axis of the head portion.

15. The device of claim 9, wherein a surface of at least one of the flanges of the locking cap is angled inwardly towards a center of the first portion for securely engaging at least one of the spaced apart slots in the head portion.

16. The device of claim 9, wherein the flanges of the first portion of the locking cap cammingly engage the spaced apart slots of the head portion upon rotation of the first portion of the locking cap with respect to the second portion.

17. The device of claim 9, wherein rotation of the first portion of the locking cap with respect to the second portion cammingly forces at least one of the flanges against at least one of the slots in the head portion.

18. A device for securing a spinal rod to the spine comprising:
   a) a head portion having first and second side walls defining a channel configured to receive a spinal rod, the head portion including a set of spaced apart slots formed in the sidewalls;
   b) a fastener portion depending from the head portion and being configured to engage bone; and
   c) a locking cap having a first portion with flanges extending outward from a body of the first portion, and a second portion rotatably coupled to the first portion, the second portion including a bottom surface with an elongate recess extending along an axis and a projection projecting in a direction transverse to the axis, the first portion of the locking cap being adapted to rotate with respect to the second portion about the projection, and the elongate recess being configured to engage the spinal rod.

19. The device of claim 18, wherein the projection is an axial post.

20. The device of claim 18, wherein rotation of the first and second portions relative to one another forces at least one of the flanges against at least one of the slots in the head portion to secure the spinal rod relative to the head portion.

21. The device of claim 20, wherein the flanges of the first portion of the locking cap cammingly engage the spaced apart slots of the head portion upon rotation of the first portion of the locking cap with respect to the second portion.

22. The device of claim 20, wherein rotation of the first and second portions relative to one another cammingly forces at least one of the flanges against at least one of the slots in the head portion.

23. The device of claim 18, wherein the second portion of the locking cap is rotatably engaged with a bottom surface of the first portion.

* * * * *